United States Patent [19]

Pesonen et al.

[11] Patent Number: 5,763,183
[45] Date of Patent: Jun. 9, 1998

[54] ALLELIC VARIATION OF THE SEROTONIN 5HT7 RECEPTOR

[75] Inventors: Ullamari Pesonen; Markku Koulu, both of Turku, Finland; Markku Linnoila, Bethesda; David Goldman, Potomac, both of Md.; Matti Virkkunen, Helsinki, Finland

[73] Assignee: The United States of America as represented by the Department of Health and Human Services, Washington, D.C.

[21] Appl. No.: 745,269

[22] Filed: Nov. 8, 1996

[51] Int. Cl.⁶ .................. C12Q 1/68; C12P 19/34; C07H 21/02; C07H 21/04
[52] U.S. Cl. .................. 435/6; 435/91.1; 435/91.2; 435/4; 435/320.1; 435/240.2; 435/252.3; 435/240.4; 435/254.11; 435/254.9; 530/350; 204/182.8; 536/23.1; 536/24.3; 536/24.32
[58] Field of Search .................. 435/6, 91.1, 91.2, 435/4, 320.1, 240.2, 252.3, 240.4, 254.11, 254.9; 530/172.3, 350; 204/182.8; 536/23.1, 24.3, 24.32

[56] References Cited

PUBLICATIONS

Pesonen et al. Neurosci. abstr., 21, Part 2, p. 1121, 1995.
Bard et al. Genbank Sequence Listing, Accession No. L 21195, 1993.
U. Pesonen, et al., *Rare non–conservative amino acid substitution in the 5–HT₇ receptor gene found in alcoholics with antisocial personaltiy disorder,* Soc. Neurosci. Abstr., 21, p. 1121, 1995.

Crowe, *Arch. Gen. Psychiatry* 31:785, 1974.

Roy et al., *Arch. Gen. psychiatry* 48:29, 1991.

Roy et al., *Prog. Neuro–Psychopharmacol. Psychiatry* 11:173, 1987.

Stoll and Goldman, *J. Neurosci. Res.* 28:457, 1991.

Roth B.L., et al. *J. Pharmacol. Exp. Ther.* 268:1403, 1994.

Linnoila, et al., *J. Clin Psychiatry* 53:10 (suppl), 1992.

Lappalainen, et al., *Genomics* 27, 274–279, 1995.

*Primary Examiner*—W. Gary Jones
*Assistant Examiner*—Dianne Rees
*Attorney, Agent, or Firm*—Knobbe, Martens, Olson & Bear, LLP

[57] ABSTRACT

An allelic variant of the 5HT7 serotonin receptor was discovered. Family study data indicate that this variant can be correlated to alchoholic offerders. DNA encoding the variant protein, the protein itself, vectors containing the variant gene and cell lines carrying a vector with the variant gene are part of the invention.

10 Claims, No Drawings

ALLELIC VARIATION OF THE SEROTONIN 5HT7 RECEPTOR

This application claims the benefit of U.S. Provisional application No. 60/006,394, filed Nov. 9, 1995.

FIELD OF THE INVENTION

This invention relates to serotonin receptors. Specifically, this invention relates to allelic variants of the serotonin 5HT$_7$ receptor.

BACKGROUND OF THE INVENTION

Family, twin and adoption studies indicate genetic vulnerability to psychiatric disorders, including antisocial personality (Crowe, *Arch. Gen. Psychiatry* 31:785, 1974), suicidal behavior (Roy et al., *Arch. Gen. Psychiatry* 48:29, 1991), panic disorder and anxiety. Family and population studies have shown that these disorders usually co-occur with alcoholism and alcohol abuse (Roy et al., *Prog Neuro-Psychopharmacol. Psychiatry* 11:173, 1987). Although psychiatric disorders often arise from a complex combination of environmental, genetic and biological factors, it may be possible to find biochemical and genetic variables that predict these behaviors and also facilitate implementation of preventative and therapeutic measures.

Several lines of evidence suggest that a lower activity of brain serotonergic pathways is related to several neuropsychiatric disorders. For example, lower levels of 5-hydroxyindoleacetic (5-HIAA), the main metabolite of serotonin (5-HT) in the cerebrospinal fluid have been reported in clinical studies of aggression, depression, impulsive crime and alcoholism. In the genetic hypothesis of these disorders, vulnerability is transmitted through inheritance of a functionally divergent allele. Variation in central serotonin function would have pleiotropic effects beyond behavior. For example, some effects would involve increasing the vulnerability to anxiety and mood disorders as well as impulsive/aggressive behaviors.

Several important genes for normal brain serotonin function have been cloned, including tryptophan hydroxylase (Stoll and Goldman, *J Neurosci. Res.* 28:457, 1991), the serotonin transporter, monoamine oxidases A and B and several serotonin receptors. In addition, serotonin receptor agonist and antagonists have been developed as drugs for treating specific neuropsychiatric disorders. Drugs with affinity for 5-HT$_2$ receptors have been used to treat schizophrenia, Parkinsonism, and anxiety disorders. Several azapirones, such as buspirone, gepirone, and ipsapirone, have high affinities for 5HT$_{1A}$ receptors in the brain, and are used to treat anxiety. For example, clozapine which is an antipsychotic drug with fewer extrapyramidal side effects is used to treat schizophrenic patients who do not respond to other drug treatments. Clozapine has a strong affinity for the serotonin 5-HT$_2$ subclass of receptors. In addition, 5-HT$_{1A}$ class agonists, such as buspirone, are effective treatments for anxiety.

Highly selective 5-HT uptake inhibitors, which have minimal effects on norepinephrine or dopamine uptake or on other neurotransmitter receptors, have been used successfully to treat depression. Naturally, characterizing all of the specific 5-HT receptors would clarify the role of serotonin in the central nervous system, and assist neuropsychiatric drug development.

Much recent interest in serotonin research has concentrated on the 5-HT$_7$ receptor. This receptor is a guanine nucleotide regulatory protein coupled receptor (GPCR) and, on the basis of its sequence, it is thought to have the typical GPCR structure of seven hydrophobic transmembrane helices separated by three extracellular and three intracellular loops. Pharmacologically, the 5-HT$_7$ receptor resembles serotonin receptors in the 5-HT$_1$ and 5-HT$_2$ families, but unlike these receptors, activation of the 5-HT$_7$ receptor stimulates adenylate cyclase. In this regard, the 5-HT$_7$ receptor resembles the 5-HT$_4$ and 5-HT$_6$ receptor subtypes.

Although studies clarifying the physiological role of the 5-HT$_7$ receptor are limited, it has been suggested that 5-HT$_7$ receptors are involved in the regulation of circadian rhythms. Circadian rhythms in mammals are known to be controlled by the suprachiasmatic nucleus of the hypothalamus and pharmacological studies suggest that the serotonin receptor subtype modulating circadian rhythms is the 5-HT$_7$ receptor.

The 5-HT$_7$ receptor also has a distinct pharmacological profile which includes high affinity for clozapine and related atypical antipsychotic agents as well as for some typical antipsychotic agents (Roth B. L., et al. *J Pharmacol. Exp. Ther.* 1994;268:1403–1410). Thus, the 5-HT$_7$ receptor may play a role in the therapeutic action of these drugs and may be involved in the pathophysiology of certain psychiatric disorders. These disorders would include antisocial personality disorder of the impulsive and explosive type that is associated with disturbances of the diurnal rhythm.

Pharmacological studies in humans have suggested that abnormal function of 5-HT$_7$ receptors might play a role in the etiology of certain disorders. Accordingly, there is a need to identify and characterize the serotonin receptors and those functional variants which associate with neuropsychiatric disorders. There is a corresponding need for assays that will permit identification of functional variants in various segments of the population. With this knowledge, receptor variant-specific drugs and diagnostic information can be developed.

SUMMARY OF THE INVENTION

We have discovered an allelic variant of the 5-HT$_7$ receptor. This variant is identical to the wildtype 5-HT$_7$ receptor except for a non-conservative amino acid change in the third intracellular loop of the protein. A substitution of a leucine in place of the normal proline residue was found in the 279th amino acid of the final protein. A cytosine (C) to thymidine (T) genetic transversion at position 863 of SEQ ID NO: 1 caused a proline to be replaced by leucine at amino acid 279 of the encoded protein (SEQ ID NO: 2).

Large scale studies determined that this non-conservative amino acid substitution (5-HT$_{7Leu279}$) was present in 3/81 Finnish alcoholic offenders with antisocial personality disorder and who also fulfilled the diagnostic criteria for intermittent explosive disorder. The variant allele was only found in 1/232 Finnish psychiatrically interviewed, unrelated controls.

The variant allele was also found in two subjects who are relatives of one offender without a Leu$_{279}$ amino acid substitution. The Proline$_{279}$ to Leucine$_{279}$ substitution of the 5HT$_7$ gene was found to be significantly associated to antisocial personality disorder in Finnish alcoholic offenders (p<0.02).

Central to the present invention is the discovery of an allelic variant of the serotonin 5HT$_7$ receptor that differs from the predominant wild-type receptor. One embodiment of the present invention relates to isolated DNA encoding that serotonin 5HT$_7$ receptor wherein the DNA encodes a leucine at amino acid position 279 of the receptor. The

3 isolated DNA may, for example, be provided in a recombinant vector. Preferably the isolated DNA has the nucleic acid sequence of SEQ ID NO:1.

Also contemplated in the present invention is an isolated protein having the amino acid sequence of a serotonin 5HT$_7$ receptor, wherein the protein has a leucine residue at amino acid position 279. Preferably, the protein has the amino acid sequence of SEQ ID NO:2.

Assays for the variant serotonin receptor have significant value, both in research relating to serotonin function and in diagnostic assays because of the correlation between behavioral disorders and this receptor. Thus, the invention includes a method for detecting the presence of DNA encoding an allelic variant of the serotonin 5HT$_7$ receptor, comprising isolating DNA encoding the serotonin 5HT$_7$ receptor, amplifying a region of the DNA that encodes amino acid number 279 of the serotonin 5HT$_7$ receptor, and determining whether the isolated DNA encodes a leucine residue at amino acid number 279, wherein a leucine residue at amino acid position 279 indicates the presence of the allelic variant of the serotonin 5HT$_7$ receptor.

In one embodiment, the amplifying step comprises polymerase chain reaction amplification. This amplifying step may advantageously use DNA primers that insert a new restriction site near the codon that encodes amino acid number 279.

The present invention further includes antibodies specific for the serotonin 5HT$_7$ allelic variant receptor protein (5HT$_{7leu}$) wherein the receptor protein has a leucine at amino acid position 279. This antibody does not bind the predominant wild type receptor. Advantageously, the antibody is a monoclonal antibody.

These antibodies, in turn, provide a method for detecting the presence of an allelic variant of the serotonin 5HT$_7$ receptor, comprising providing a biological sample containing the serotonin 5HT$_7$ receptor, contacting the sample with an antibody which specifically binds to a serotonin 5HT$_7$ receptor with a leucine residue located at amino acid position 279, and detecting the binding of the antibody to the receptor, wherein detectable binding indicates the presence of an allelic form of the serotonin 5HT$_7$ receptor. Preferably, the cells are human, and may be brain cells. Labeled antibody is particularly useful, including radiolabeled antibody and fluorescent antibody. With fluorescent antibody, the detecting step can comprise fluorescence activated cell sorting.

The present invention also includes a method for detecting the presence of an allelic variant of the serotonin 5HT$_7$ receptor by 1) providing a biological sample containing the serotonin 5HT$_7$ receptor; 2) contacting the sample with an antibody which specifically binds to a serotonin 5HT$_7$ receptor having a leucine residue located at amino acid position 279, and wherein said antibody does not bind a 5HT$_7$ receptor having a proline residue at position 279; 3) detecting the absence of binding of said antibody to said receptor, wherein lack of detectable binding indicates the presence of an allelic form of the serotonin 5HT$_7$ receptor.

As discussed above, a strong correlation exists between the serotonin family of receptors and some neuropsychiatric diseases. For this reason it is important to identify as many of the serotonin receptor variants as possible. Investigators looking for drugs that affect the quantity of serotonin byproducts need to have methods for testing their candidates against all serotonin receptors. Thus, the 5-HT$_{7leu}$ variant and associated DNA and assays provide important investigative tools for both behavioral research and the screening of neuropsychiatric drug candidates.

4
DETAILED DESCRIPTION

We discovered that the allelic variation which includes leucine at position 279 (Leu279) of the 5-HT$_7$ receptor protein may be associated with several antisocial personality disorders in connection with other personality disorders in Finnish alcoholics. Leu279 is a rare allele and it is relatively uncommon even in alcoholics with antisocial personality disorder.

The Pro$_{279}$ to Leu$_{279}$ substitution occurred in the putative third intracellular loop of the 5-HT$_7$ receptor protein. The third intracellular loop exhibits the highest diversity within the family of homologous G-Protein coupled receptors (CPCRs). However, structure-function analysis of several GPCRs has suggested that the third intracellular loop has binding regions with specificity for various G-protein subunits. In addition, the third intracellular loop contains sites for receptor phosphorylation.

As is known, a proline to leucine substitution can alter the secondary structure of protein. Proline residues are mostly found in bends and are known to break helices by introducing kinks. Leucine residues preferentially form helices or sheets. Evidence from studies of several GPCRs indicate that the regions of the third intracellular loop close to the transmembrane segments interact with the a-subunit of G-proteins.

Within the 5-HT$_7$ receptor, the protein sequence which follows the Pro$_{279}$ residue is much less well conserved than the region which immediately precedes it. Thus, it is possible that the Pro$_{279}$ residue terminates a conserved helical segment positioned at the intracellular end of the fifth transmembrane segment. Modelling of the secondary structure of the 5-HT$_7$ receptor protein using software from the University of Wisconsin Genetics Computer Group (UWGCG, ver. 7, Madison, Wis.) predicts that a Leu279 substitution would result in decreased in hydrophilicity and increased likelihood of helix formation. Thus, the most likely consequence of the Pro$_{279}$→Leu$_{279}$ amino acid substitution is a change in local protein structure that could affect G-protein coupling. Such an alteration at the molecular level could be sufficient to modify the function of the 5-HT$_7$ receptor and bring about behavioral differences.

The present invention includes our discovery of the 5-HT$_{7leu}$ gene (SEQ ID NO:1) along with the corresponding variant protein product (SEQ ID NO:2) of this gene. In addition, antibodies that can distinguish between the two 5-HT$_7$ forms are within the scope of the present invention.

One of ordinary skill in the art will appreciate that a kit can be produced that contains all the necessary components to identify a carrier of the 5HT$_{7leu}$ gene. This kit would include PCR primers, PCR enzymes, restriction enzymes and any other component useful for determining the one base pair change at position 863 between the wildtype gene and the allelic variant.

It should also be appreciated that one could identify the nucleic acid change between the wildtype and the variant 5-HT$_7$ receptor by well known hybridization techniques. Under known conditions, a one base pair mismatch can be determined by, for example, Southern blot analysis or in situ hybridization.

The present invention, thus, includes isolated or purified 5-HT$_{7leu}$ receptor; DNA encoding that receptor; antibodies with specific binding to the 5-HT$_{7leu}$ receptor and assays for detecting the receptor. In addition, expression vectors encoding 5-HT$_{7leu}$ and cells expressing the recombinant expression vector are also anticipated. Further, kits and assays for determining the presence or absence of the variant receptor are a part of the present invention.

There is an established need for assays useful in correlating behavioral patterns with chemical differences in individuals, and such an assay for the present serotonin variant will be a valuable tool in neuropsychiatric investigations. The isolated or purified protein is useful, inter alia, in competitive assays and in preparation of monoclonal and polyclonal antibody against the variant receptor. An additional facet of the present invention is provision of assays for compounds that bind or block binding to the 5-HT$_{7leu}$ receptor. Each of these embodiments is discussed in more detail in the following examples.

Another application of our discovery is screening individual carriers of the variant gene. Correlations between the allelic variant and neuropsychiatric disorders lead to the necessity of providing screening techniques for identifying carriers of the variant allele.

As a first step we analyzed the 5-HT$_7$ receptor gene for variants in a population of alcoholics.

EXAMPLE 1

Detection of the 5-HT$_{7leu}$ Variant Allele by Single Stranded Conformational Polymorphism The 5-HT$_7$ variant was originally identified by single strand conformational polymorphism (SSCP) analysis of DNA taken from over one hundred patients. These patients were selected for analysis because they showed behavioral and neurochemical evidence of altered serotonin function. Thus, the primary population for screening was Finnish alcoholic offenders and Finnish controls. Many of these alcoholics have low serotonin turnover and impulsive antisocial behavior. The primers used to amplify DNA from these patients are shown below.

Upstream: 5'-GAT TCT CTC CGT CTG GCT TCT—3' (SEQ ID NO:3)

Downstream: 5'—TGC GAT AGG TGG TCC TCA GGT—3' (SEQ ID NO:4)

Cell lines were derived from individual patients by immortalizing lyphoblastoid cells with Epstein Barr virus. DNA samples were taken from these immortalized cell lines using standard protocols.

The PCR reaction mix contained 100 µg genomic DNA isolated from immortalized cell lines, 0.8 mM dNTPs, 0.5 µM primers, 0.15 mM [$\alpha^{33}$P]—dCTP, 0.25 U of AMPLI-TAQ® POLYMERASE (Perkin Elmer Cetus, Norwal, Conn.), 60 mM Tris-HCl (pH 8.5), 15 mM (NH$_4$)SO$_4$, 1.5 MM MgCl$_2$ in a total volume of 5 µl.

Samples were amplified using a GeneAmp® PCR System 9600 (Perkin Elmer Cetus, Norwalk, Conn.) for 30 cycles consisting of 30 seconds at each of three temperatures: 95° C., 55° C. and 72° C. After amplification, a solution containing 95% formamide, 10 mM NaOH, 0.05% xylene cyanol and 0.05% bromphenol blue were added for a total volume of 25 µl. After denaturation at 95° C. for 3 minutes, 3.5 µl of the mixture was loaded on a MDE™ Gel (AT Biochem, Malvern, Pa.) and electrophoresis was performed at room temperature for 16 hours at 4 watts. The gel was dried exposed to Kodak XAR film for 12 hours at room temperature.

A 302 base pair DNA fragment was amplified by SSCP and corresponded to nucleotides 633–935 of the published cDNA sequence (SEQ ID NO:1). The PCR products were nucleic acid sequenced by direct thermal cycle dideoxy sequencing (CircumVent™, New England Biolabs, Beverly, Mass.). Since the restriction enzyme XhoI leaves the 5HT$_{7pro}$ DNA sequence yielding two fragments (230 bp and 72 bp) but leaves the 5HT$_{7leu}$ DNA sequence uncut (302 bp), the XhoI site was used in a PCR-restriction fragment length polymorphism (RFLP) analysis. Fragments were visualized by electrophoresis in 1.5% agarose gel electrophoresis and ethidium bromide staining.

We found that several of the patients in this group had an allelic variation in a specific region of the 5HT$_7$ gene. Thus, we undertook a more specific experiment designed to characterize this variation.

To provide an additional assay for determining carriers of the 5-HT$_{7leu}$ variant, we performed nucleic acid sequencing reactions of the amplified PCR fragments described above. However, one of ordinary skill in the art will appreciate that many ways are available to directly determine the nucleic acid sequence of DNA fragments.

The PCR product was purified by agarose gel electrophoresis followed by extraction with glass beads (Geneclean™, BIO 101, La Jolla, Calif.). DNA was directly sequenced by dideoxy cycle-sequencing according to the manufacturers' instructions (Life Technologies, Gaithersburg, Md.). Through this sequencing we confirmed that a C→T substitution had been made at nucleotide 863 of the 5HT$_7$ gene (SEQ ID NO:1). To further confirm these findings, a large scale experiment was undertaken to discover any associations with this new allele and certain psychological disorders.

EXAMPLE 2

Screening of Samples for the 5-HT$_{7leu}$ Variant Allele using Allele Specific Amplification A detailed description of the subjects and the study protocol are presented elsewhere (3). Briefly, subjects included in the study are alcoholic offenders who were ordered to undergo forensic psychiatric examination. The controls are a random sample of healthy volunteers of socioeconomic background similar to the offenders. All the subjects were interviewed by a research psychiatrist using the Structured Clinical Interview (SCID) I and II for DSM-II-R. Additionally, each subject was administered a structured interview covering the DSM-III diagnosis for intermittent explosive disorder. All interviews were checked for errors and omissions by a research social worker. The interviews were then blind rated by two research psychiatrists and any conflicts were settled in a consensus meeting attended by a senior research psychiatrist.

The alcoholic offender group (n=177) was divided into two subgroups of those individuals with antisocial personality disorder (ASP) (n=81) or "other alcoholic offenders" (n=96). All subjects have a written informed consent and the study protocol was approved by the Department of Psychiatry and Helsinki University Central Hospital Institutional Review Boards of Finland. In the United States, the protocol was approved by the National Institutes of Mental Health Institutional Review Board and the Office for Protection from Research Risks.

Allele specific amplification (ASA) was used to rapidly screen large numbers of samples for the 5-HT$_{7leu}$ variant allele. In this study, the genotypes of 177 Finnish alcoholic offenders and 232 Finnish psychiatrically interviewed, unrelated controls and 325 relatives of alcoholics were determined.

For ASA, the PCR reaction was run with an allele specific upper primer (SEQ ID NO: 5) and a lower primer recognizing both alleles (SEQ ID NO: 6)

5'—ACA AGT TTC CTG GCT TCC T—3'(SEQ ID NO:5)

5'—GCT GCG ATA GGT GGT CCT CAG GT—3'(SEQ ID NO:6)

The annealing temperature for this reaction was 68° C. and PCR products were thereafter separated on a 7.5% polyacrylamide gel. The appearance of a band at 351 bp was considered to be evidence of a positive allele-specific reaction. All positive samples were confirmed by RFLP analysis as explained above in Example 1 which also detected heterozygosity.

This rare non-conservative amino acid substitution ($5\text{-HT}_{7leu279}$) was observed in 3/81 Finnish alcoholic offenders with antisocial personality disorder and who also fulfilled the diagnostic criteria for intermittent explosive disorder, and 1/232 Finnish psychiatrically interviewed, unrelated controls. We have also found the variant in two subjects who are relatives of one offender without Leu279 amino acid substitution (TABLE 1).

TABLE 1

Frequencies of $5\text{-HT}_7$ genotypes in Finnish psychiatrically interviewed unrelated controls and alcoholic offenders.

| Subjects: | Pro279/Pro279 | Pro279/Leu 279 | Frequency |
|---|---|---|---|
| Psychiatrically interviewed unrelated controls | 231 | 1 | 0.004 |
| Antisocial personality disorder | 78 | 3 | 0.038* |
| Other alcoholic offenders | 96 | 0 | 0.000 |

All offenders had the DSM-III diagnosis of either alcohol abuse or alcohol dependence. *Chi-square $p < 0.02$ vs. controls ($X^2 = 7.879$, DF = 2).

Although the Leu279 allele was found to be rare, with only six heterozygotes were detected, it was observed significantly more often in alcoholics and relatives of alcoholics with related problems. Also, the three alcoholics with this rare amino acid substitution had multiple personality disorder including intermittent explosive disorder.

The results of this experiment demonstrated a significant association between the proline$_{279}$ to leucine$_{279}$ substitution and antisocial personality disorder in Finnish alcoholic offenders ($p < 0.02$).

As shown in Table 2, the two relatives (521 and 523) with the Leu279 variant included one who was alcoholic and an other who had attempted suicide. However, both were relatives of an alcoholic offender who was not carrying Leu279. Although the relatives of the three alcoholic offenders with Leu279 are not available for analysis at this time, the present study does provide the first evidence on the involvement of an inherited variant of the serotonin $5\text{-HT}_7$ receptor gene in a psychiatric disorder and more specifically links this variant with a subgroup of alcoholic offenders with antisocial personality disorders and other personality disorders.

TABLE 2

Characteristics of six subjects who were Pro279/Leu279 heterozygotes at the $5\text{-HT}_7$ receptor gene.

| Sex: | Age/Year: | Diagnosis: | Subject and Category: | Notes: |
|---|---|---|---|---|
| Male | 21 | AD,DD,OD,BP, ASP,IED | Alcoholic offender | Alcoholic father and mother |
| Male | 44 | AD,NA,BP,ASP, IED | Alcoholic offender | Alcoholic father |
| Male | 37 | AD,OD,SP,IED | Alcoholic offender | Alcoholic father |
| Female | 49 | — | Relative | Mother of alcoholic offender, a history of suicide attempt |
| Male | 30 | AA | Relative | Brother of alcoholic offender, alcohol abuse |
| Male | 24 | — | Control | Student |

AD = alcohol dependence, AA = alcohol abuse, DD = drug dependence, OD = other DSM-III-R disorder, NA = narcissistic personality disorder, BP = borderline personality disorder, ASP = antisocial personality disorder, SP = schizoid personality disorder, IED = intermittent explosive disorder. Diagnoses were made by DSM-III-R criteria except for IED, which was by DSM-III criteria.

To test the distribution of genotypes, the Chi-square test with two-tailed probability was used (BMDP/Dynamic Release 7.0, BMDP Statistical Software, Cork, Ireland).

Although the frequency of this polymorphism is low and all the affected patients are heterozygous, the rare allele Leu$_{279}$ was found more often in alcoholic offenders with antisocial personality disorder ($p < 0.02$). Leu$_{279}$ was also found in normal controls, but only one heterozygote was found among 232 healthy, psychiatrically interviewed Finnish controls (allele frequency 0.002). The total number of DNA samples screened for this mutation was 734, but most of them were relatives (n=325) of alcoholic offenders (n=177) and they were not included in the association analysis. The relatives group does not include the relatives of the three alcoholic offenders with Leu$_{279}$ because these families were unavailable for this study.

The detailed psychiatric diagnoses of the individuals with Leu279 are presented in Table 2. Three of them were alcoholic offenders, two were relatives of an offender and one was a control. Among three alcoholic offenders several biochemical parameters, including concentrations of CSF 5-HIAA, homovanillic acid, 3-methoxy-4-hydroxyphenylglycol, and concentrations of CSF hormones (testosterone, arginine vasopressin, adrenocorticotrophin, day/night cortisol), did not clearly differ from alcoholic offenders without the polymorphism (data not shown). However, all three of the alcoholic offenders with Leu$_{279}$ had antisocial personality disorder and fulfilled additional criteria for multiple psychiatric diagnoses including intermittent explosive disorder. Thus, we found that the Leu$_{279}$ allele of the $5\text{-HT}_7$ receptor gene could be involved in a specific subtype of alcoholism associated with antisocial personality disorder.

To determine whether other primate species carried the Leu$_{279}$ allele, we sequenced this region of the $5\text{-HT}_7$ gene in an orangutan and a chimpanzee. These sequences were compared with rat and human $5\text{-HT}_7$ genes to determine if proline at position 279 was conserved. We discovered that the amino acid residue proline was conserved at position 279 and is located at the C-terminal end of a stretch of residues that is invariant across all three primates and the rat.

EXAMPLE 3

Production of Antibodies Against the $5\text{-HT}_{7leu}$ Variant Receptor Protein Cells expressing the 5-HT$_{7leu}$ variant receptor are obtained from human CSF and lysed with NP40, and the isolated membranes are injected into rabbits. The lysed membranes are isolated in a non-ionic detergent so as not to affect the membrane bound receptors. Freund's adjuvant is used in the injection to help stimulate an antigenic response by the rabbits using well known methods. After two booster shots of the lysed membranes, the rabbits are bled and the sera isolated by centrifugation.

The antibodies in the crude rabbit sera extract are $^{125}$I labeled by well-known methods and tested for activity against transformed COS7 cells expressing the variant receptor. COS7 cells expressing the wildtype allele are used to preabsorb antibodies with nonspecific binding. A Western blot having one lane containing protein lysates from COS7 cells expressing the variant gene, and a second lane having lysates from COS7 cells expressing the wildtype 5-HT$_7$ receptor (control) is run.

Monoclonal antibodies can be made by well known methods in addition to the polyclonal antibodies discussed above. One method of producing monoclonal antibodies is discussed below.

These antibodies will specifically recognize the variant 5-HT$_{7leu}$ receptor protein on cell membranes. Antibodies of this type can be used as research tools to characterize expression of this variant on different cells or in different populations or under different physiological conditions. Antibodies can further be used as a diagnostic of abnormal conditions linked to expression of the variant 5-HT$_{7leu}$ receptor.

EXAMPLE 4

Production of Monoclonal Antibodies Against the 5-HT$_{7leu}$ Variant Receptor Protein Cells expressing the 5-HT$_{7leu}$, receptor are isolated from human CSF and lysed with NP40. The cell membranes are pelleted by centrifugation and isolated membranes having bound 5-HT$_{7leu}$, variant receptor proteins are injected in Freunds adjuvant into mice. After being injected 9 times over a three week period, the mice spleens are removed and following conventional cell separation techniques were resuspended in PBS.

The suspended spleen cells are mixed (approximately 4:1) with SP 2/0 Myeloma cells. Polyethylene glycol is added to fuse the myeloma cells to the spleen cells, and the fused cells are selected in HAT media. The fused cells are aliquoted so that only one cell is grown in each well of a 96-well microtiter plate. Each cell is grown, the media removed and secreted proteins in the media are $^{125}$I or fluorescently labeled. The labeled media from each well is used to probe a Western blot of cell lysates having the 5-HT$_{7leu}$, variant and the 5-HT$_{7pro}$ (wildtype) receptor. The desired fusion cell will produce a monoclonal antibody that strongly binds the 5-HT$_{7leu}$, variant receptor lane on the Western blot, but doesn't bind to a similar sized protein in the 5-HT$_{7pro}$ (control) lane.

It will be appreciated by those skilled in the art that a monoclonal antibody that specifically recognizes the 5-HT$_{7pro}$ form of the receptor but does not recognize the variant 5-HT$_{7leu}$ receptor could also be used to detect the presence of the variant. That is, such a monoclonal antibody would give a negative response with receptors from a homozygotic person for the 5-HT$_{7leu}$ allele while giving a positive response with a 5-HT$_{7pro}$ control.

These monoclonal antibodies provide a way of detecting expression of the 5-HT$_{7leu}$ variant serotonin receptor protein. Another method of detecting expression of the 5-HT$_{7leu}$ variant is by in situ hybridization.

EXAMPLE 5

In Situ Hybridization Using 5-HT$_{7leu}$ Variant Gene Fragments

In situ hybridization allows the identification of mRNA within intact tissues, including from human brain biopsies. In this method, oligonucleotides corresponding to a portion of the 5-HT$_{7leu}$ variant gene (SEQ ID NO: 1) are used to detect specific mRNA species in the brain.

Biopsied brain tissue is perfused with a 4% formaldehyde solution using standard histology methods. The brain tissue is frozen with liquid nitrogen and cut into 5 μm to 30 μm sections that are placed on slides and incubated in proteinase K for approximately 15 minutes. The slides are then rinsed in diethylpyrocarbonate-treated water, and ethanol, and placed in a prehybridization buffer.

A radioactive probe corresponding to the PCR product obtained from using primers SEQ ID NO:3 and SEQ ID NO:4 is made by performing the PCR using [$\alpha^{32}$P]dCTP in the reaction mixture. The labeled PCR product is incubated with the sectioned brain tissue using standard hybridization methods. After incubation and washing at a temperature that allows binding to the 5-HT$_{7leu}$ variant mRNA but not to the 5-HT$_{7pro}$ wildtype mRNA, the slides are air dried and labeled areas are visualized by autoradiography. Dark spots on the tissue sample indicate hybridization of the probe with the brain mRNA thereby demonstrating expression of the 5-HT$_{7leu}$ variant receptor.

EXAMPLE 6

Ligand Binding to 5-HT$_{7leu}$ and 5-HT$_{7pro}$ Receptors In Human Cells

Cells expressing the 5-HT$_{7leu}$ or 5-HT$_{7pro}$ receptors are isolated from human tissue, including from brain biopsies or cells isolated from CSF, using commonly known methods. The cells are incubated with known or suspected ligands for sufficient time and in sufficient concentrations to allow binding to the 5-HT$_7$ receptors, employing commonly used methods for determining binding in vitro. Known or suspected ligands include 5-HT analogs, 5-HT antagonists, and various pharmacological drugs used to treat neuropsychiatric disorders. Ligands are labeled either radioactively or fluorescently and relative binding of the ligand to the 5-HT$_7$ receptors is measured by measuring the amount of radioactivity or fluorescence attached to the membranes after the unbound fraction is washed away.

The relative binding efficiencies of ligands may be useful in developing new drugs to treat certain clinical conditions, or in determining effective drug dosages for clinical treatment of individuals with variant 5-HT$_7$ receptors.

EXAMPLE 7

Transfection of Mammalian Cells with the 5-HT$_{7leu}$ and 5-HT$_{7pro}$ Receptor Genes Expression of the two forms of the 5-HT$_7$ serotonin receptor is assayed in mammalian COS7 or CHO cells transfected with the genes encoding the 5-HT$_{7pro}$ or 5-HT$_{7leu}$ receptor proteins in an expression plasmid, pSRα. The 5-HT$_{7pro}$ and 5-HT$_{7leu}$ genes individually are subcloned into the expression vector pSRα by using standard molecular cloning methods. The transfected COS7 cells are then placed in media for about 72 hours to allow expression of the 5-HT$_{7pro}$ or 5-HT$_{7leu}$ receptors on their cell surface.

COS7 cells are transiently transfected with the pSRα-5-HT$_{7pro}$ or pSRα-5-HT$_{7leu}$ construct using the calcium phosphate precipitation method as previously described by Monsma, F. J. et al., *Proc. Natl. Acad. Sci. USA* 87:6723, 1990. Cells are harvested 72 hours after transfection and either used directly or the membranes containing the 5-HT$_7$ receptors are isolated from the cells using methods described below.

Cells or membranes isolated from them are used to assay binding of various ligands of pharmacological interest. The relative binding efficiencies of ligands are useful in developing new drugs to treat clinical conditions associated with 5-HT$_7$ receptors.

While COS7 cells are a preferred embodiment, those skilled in the art will appreciate that other cells and vectors could be used in transfection for expression of the 5-HT$_7$ receptor genes.

EXAMPLE 8

Ligand Binding to Mammalian Cells Transfected with the 5-HT$_{7pro}$ and 5-HT$_{7leu}$ Receptor Genes Mammalian COS7 cells are transfected as described above, and binding of ligands to the 5-HT$_{7pro}$ or 5-HT$_{7leu}$ serotonin receptors is assayed using whole cells expressing the 5-HT$_{7pro}$ or 5-HT$_{7leu}$ receptors on their surface.

Cells are collected 72 hours after transfection and placed in fresh media containing radiolabeled or fluorescently labeled ligands. Ligands include 5-HT analogs, 5-HT antagonists, and various pharmacological drugs used to treat neuropsychiatric disorders. After incubation for various times to allow binding of the ligands to the 5-HT$_7$ receptors, cells are washed and then assayed for binding of the ligand to the cells, employing commonly used methods for detecting radioactivity or fluorescence.

This method is useful because cells that express 5-HT$_7$ receptors can be obtained with relative ease without relying on clinical samples. Mammalian COS7 cells probably reflect the physiological conditions normally affecting expression of serotonin receptors in humans. The relative binding efficiencies of ligands are useful in developing new drugs to treat clinical conditions associated with 5-HT$_7$ receptors, or in determining effective drug dosages for clinical treatment of individuals with specific genotypes for the 5-HT$_7$ receptor.

EXAMPLE 9

Ligand Binding to Membranes Isolated from Mammalian Cells Transfected with the 5-HT$_{7pro}$ and 5-HT$_{7leu}$ Receptor Genes Mammalian COS7 cells are transfected as described above, and binding of ligands to the 5-HT$_{7pro}$ or 5-HT$_{7leu}$ serotonin receptors is assayed using membranes isolated from cells expressing the 5-HT$_{7pro}$ or 5-HT$_{7leu}$ receptors on their surface. Cells are harvested 72 hours after transfection and either disrupted in a bounce homogenizer in 50 mM Tris-HCl, pH 7.4 at 37° C., 10 mM MgSO$_4$ and 0.5 mM EDTA, or frozen in 5 mM Tris-HCl, pH 7.4 at 25° C., 5 mM MgCl$_2$, 250 mM sucrose and stored in liquid N$_2$ prior to membrane preparation. Crude membranes are prepared from cell homogenates by centrifugation at 43,000×g, and re-suspension in homogenization buffer at a protein concentration of 60 μg/ml.

Once the crude membranes are prepared from the cell homogenates, screening of various pharmacologically indicated ligands for differential binding to the 5-HT$_{2C}$ receptors is performed as discussed above. Ligands, which are radiolabeled or fluorescently labeled, include 5-HT analogs, 5-HT antagonists, and various pharmacological drugs used to treat neuropsychiatric disorders.

This method is useful because it provides a ready source of serotonin receptors expressed on mammalian cells for comparison of many different ligands, alone or in combination, under identical binding conditions. The information from the assay relating to relative binding efficiencies of ligands is useful in developing new drugs to treat certain clinical conditions associated with expression of the different forms of the 5-HT$_7$ receptor.

---

We claim:

1. An isolated DNA sequence that codes for an allelic variant of the serotonin 5HT7 receptor having the sequence of SEQ ID NO: 1.

2. A vector containing the isolated DNA of claim 1.

3. A method for detecting the presence of DNA that codes for a $5HT_{7leu}$ allelic variant comprising:
   (a) providing a sample of human DNA;
   (b) amplifying said DNA with primers capable of amplifying a sequence encoding the third intracellular loop of the human $5HT_7$ gene; and
   (c) detecting the presence of DNA that codes for a $5HT_{7leu}$ allelic variant by determining whether the sequence of the amplified DNA comprises a sequence encoding the third intracellular loop of the human $5HT_{7leu}$ gene in which a cytosine to thymidine genetic transversion converts a proline codon to a leucine codon.

4. The method of claim 3 wherein said amplifying step (b) comprises polymerase chain reaction amplification.

5. The method of claim 3 wherein amplified DNA of the $5HT_{7leu}$ gene may be distinguished from amplified DNA of the $5HT_7$ gene by restriction fragment polymorphism analysis.

6. The method of claim 5 wherein said restriction fragment polymorphism analysis comprises digesting said amplified DNA with XhoI.

7. The method of claim 5 wherein said DNA primers are SEQ ID NOS: 3 and 4.

8. The method of claim 5 wherein said detecting step (c) further comprises restriction enzyme digestion followed by gel electrophoresis.

9. The method of claim 3 wherein said detecting step further comprises nucleic acid sequencing of the amplified DNA.

10. Host cells containing the vector of claim 2.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1406 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 28...1062
        ( D ) OTHER INFORMATION: 1

( x i ) SEQUENCE DESCRIPTION: SEQ ID NO:1:

```
CCATGGGCAG  CGGCACACGG  CGGCGCG  ATG  ATG  GAC  GTT  AAC  AGC  AGC  GGC  CGC      54
                                Met  Met  Asp  Val  Asn  Ser  Ser  Gly  Arg
                                 1                    5
```

-continued

| | | | | | | | | | | | | | | | |
|---|---|---|---|---|---|---|---|---|---|---|---|---|---|---|---|
| CCG | GAC | CTC | TAC | GGG | CAC | CTC | CGC | TCT | TTC | CTT | CTG | CCA | GAA | GTG | GGG | 102 |
| Pro | Asp | Leu | Tyr | Gly | His | Leu | Arg | Ser | Phe | Leu | Leu | Pro | Glu | Val | Gly |
| 10 | | | | | 15 | | | | | 20 | | | | | 25 |
| CGC | GGG | CTG | CCC | GAC | TTG | AGC | CCC | GAC | GGT | GGC | GCC | GAC | CCG | GTC | GCG | 150 |
| Arg | Gly | Leu | Pro | Asp | Leu | Ser | Pro | Asp | Gly | Gly | Ala | Asp | Pro | Val | Ala |
| | | | | 30 | | | | | 35 | | | | | 40 | |
| GGC | TCC | TGG | GCG | CCG | CAC | CTG | CTG | AGC | GAG | GTG | ACA | GCC | AGC | CCG | GCG | 198 |
| Gly | Ser | Trp | Ala | Pro | His | Leu | Leu | Ser | Glu | Val | Thr | Ala | Ser | Pro | Ala |
| | | | 45 | | | | | 50 | | | | | 55 | | |
| CCC | ACC | TGG | GAC | GCG | CCC | CCG | GAC | AAT | GCC | TCC | GGC | TGT | GGG | GAA | CAG | 246 |
| Pro | Thr | Trp | Asp | Ala | Pro | Pro | Asp | Asn | Ala | Ser | Gly | Cys | Gly | Glu | Gln |
| | | 60 | | | | | 65 | | | | | 70 | | | |
| ATC | AAC | TAC | GGC | AGA | GTC | GAG | AAA | GTT | GTG | ATC | GGC | TCC | ATC | CTG | ACG | 294 |
| Ile | Asn | Tyr | Gly | Arg | Val | Glu | Lys | Val | Val | Ile | Gly | Ser | Ile | Leu | Thr |
| | 75 | | | | | 80 | | | | | 85 | | | | |
| CTC | ATC | ACG | CTG | CTG | ACG | ATC | GCG | GGC | AAC | TGC | CTG | GTG | GTG | ATC | TCC | 342 |
| Leu | Ile | Thr | Leu | Leu | Thr | Ile | Ala | Gly | Asn | Cys | Leu | Val | Val | Ile | Ser |
| 90 | | | | | 95 | | | | | 100 | | | | | 105 |
| GTG | TGC | TTC | GTC | AAG | AAG | CTC | CGC | CAG | CCC | TCC | AAC | TAC | CTG | ATC | GTG | 390 |
| Val | Cys | Phe | Val | Lys | Lys | Leu | Arg | Gln | Pro | Ser | Asn | Tyr | Leu | Ile | Val |
| | | | | 110 | | | | | 115 | | | | | 120 | |
| TCC | CTG | GCG | CTG | GCC | GAC | CTC | TCG | GTG | GCT | GTG | GCG | GTC | ATG | CCC | TTC | 438 |
| Ser | Leu | Ala | Leu | Ala | Asp | Leu | Ser | Val | Ala | Val | Ala | Val | Met | Pro | Phe |
| | | | 125 | | | | | 130 | | | | | 135 | | |
| GTC | AGC | GTC | ACC | GAC | CTC | ATC | GGG | GGC | AAG | TGG | ATC | TTT | GGA | CAC | TTT | 486 |
| Val | Ser | Val | Thr | Asp | Leu | Ile | Gly | Gly | Lys | Trp | Ile | Phe | Gly | His | Phe |
| | | 140 | | | | | 145 | | | | | 150 | | | |
| TTC | TGT | AAT | GTC | TTC | ATC | GCC | ATG | GAC | GTC | ATG | TGC | TGC | ACG | GCC | TCG | 534 |
| Phe | Cys | Asn | Val | Phe | Ile | Ala | Met | Asp | Val | Met | Cys | Cys | Thr | Ala | Ser |
| | | 155 | | | | | 160 | | | | | 165 | | | |
| ATC | ATG | ACC | CTG | TGC | GTG | ATC | AGC | ATT | GAC | AGG | TAC | CTT | GGG | ATC | ACA | 582 |
| Ile | Met | Thr | Leu | Cys | Val | Ile | Ser | Ile | Asp | Arg | Tyr | Leu | Gly | Ile | Thr |
| 170 | | | | | 175 | | | | | 180 | | | | | 185 |
| AGG | CCC | CTC | ACA | TAC | CCT | GTG | AGG | CAG | AAT | GGG | AAA | TGC | ATG | GCG | AAG | 630 |
| Arg | Pro | Leu | Thr | Tyr | Pro | Val | Arg | Gln | Asn | Gly | Lys | Cys | Met | Ala | Lys |
| | | | | 190 | | | | | 195 | | | | | 200 | |
| ATG | ATT | CTC | TCC | GTC | TGG | CTT | CTC | TCC | GCC | TCC | ATC | ACC | TTA | CCT | CCA | 678 |
| Met | Ile | Leu | Ser | Val | Trp | Leu | Leu | Ser | Ala | Ser | Ile | Thr | Leu | Pro | Pro |
| | | | 205 | | | | | 210 | | | | | 215 | | |
| CTC | TTT | GGA | TGG | GCT | CAG | AAT | GTA | AAT | GAT | GAT | AAG | GTG | TGC | TTG | ATC | 726 |
| Leu | Phe | Gly | Trp | Ala | Gln | Asn | Val | Asn | Asp | Asp | Lys | Val | Cys | Leu | Ile |
| | | 220 | | | | | 225 | | | | | 230 | | | |
| AGC | CAG | GAC | TTT | GGC | TAT | ACG | ATT | TAC | TCT | ACC | GCA | GTG | GCA | TTT | TAT | 774 |
| Ser | Gln | Asp | Phe | Gly | Tyr | Thr | Ile | Tyr | Ser | Thr | Ala | Val | Ala | Phe | Tyr |
| | 235 | | | | | 240 | | | | | 245 | | | | |
| ATC | CCC | ATG | TCC | GTC | ATG | CTT | TTC | ATG | TAC | TAC | CAG | ATT | TAC | AAG | GCT | 822 |
| Ile | Pro | Met | Ser | Val | Met | Leu | Phe | Met | Tyr | Tyr | Gln | Ile | Tyr | Lys | Ala |
| 250 | | | | | 255 | | | | | 260 | | | | | 265 |
| GCC | AGG | AAG | AGT | GCT | GCC | AAA | CAC | AAG | TTT | CCT | GGC | TTC | CTT | CGA | GTG | 870 |
| Ala | Arg | Lys | Ser | Ala | Ala | Lys | His | Lys | Phe | Pro | Gly | Phe | Leu | Arg | Val |
| | | | | 270 | | | | | 275 | | | | | 280 | |
| GAG | CCA | GAC | AGC | GTC | ATC | GCC | CTG | AAT | GGC | ATA | GTG | AAG | CTC | CAG | AAG | 918 |
| Glu | Pro | Asp | Ser | Val | Ile | Ala | Leu | Asn | Gly | Ile | Val | Lys | Leu | Gln | Lys |
| | | | 285 | | | | | 290 | | | | | 295 | | |
| GAG | GTG | GAA | GAG | TGT | GCA | AAC | CTT | TCG | AGA | CTC | CTC | AAG | CAT | GAA | AGG | 966 |
| Glu | Val | Glu | Glu | Cys | Ala | Asn | Leu | Ser | Arg | Leu | Leu | Lys | His | Glu | Arg |
| | | 300 | | | | | 305 | | | | | 310 | | | |
| AAA | AAC | ATC | TCC | ATC | TTT | AAG | CGA | GAA | CAG | AAA | GCA | GCC | ACC | ACC | CTG | 1014 |
| Lys | Asn | Ile | Ser | Ile | Phe | Lys | Arg | Glu | Gln | Lys | Ala | Ala | Thr | Thr | Leu |
| | | 315 | | | | | 320 | | | | | 325 | | | |

| GGG | ATC | ATC | GTC | GGG | GCC | TTT | ACC | GTG | TGC | TGG | CTG | CCA | TTT | TTC | CTC | CT | 1064 |
|-----|-----|-----|-----|-----|-----|-----|-----|-----|-----|-----|-----|-----|-----|-----|-----|----|------|
| Gly | Ile | Ile | Val | Gly | Ala | Phe | Thr | Val | Cys | Trp | Leu | Pro | Phe | Phe | Leu |    |      |
| 330 |     |     |     |     | 335 |     |     |     |     | 340 |     |     |     |     | 345 |    |      |

CTCGACAGCC AGACCCTTCA TCTGTGGCAC TTCCTGCAGC TGCATCCCAC TGTGGGTGGA 1124

GAGGACATTT CTGTGGCTAG GCTATGCAAA CTCTCTCATT AACCCTTTTA TATATGCCTT 1184

CTTCAACCGG GACCTGAGGA CCACCTATCG CAGCCTGCTC CAGTGCCAGT ACCGGAATAT 1244

CAACCGGAAG CTCTCAGCTG CAGGCATGCA TGAAGCCCTG AAGCTTGCTG AGAGGCCAGA 1304

GAGACCTGAG TTTGTGCTAC AAAATGCTGA CTACTGTAGA AAAAAAGGTC ATGATTCATG 1364

ATTGAAAGCA GAACAATGGA GAGGAATTCG ATATCAAGCT TA 1406

( 2 ) INFORMATION FOR SEQ ID NO:2:

( i ) SEQUENCE CHARACTERISTICS:
        ( A ) LENGTH: 345 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

| Met | Met | Asp | Val | Asn | Ser | Ser | Gly | Arg | Pro | Asp | Leu | Tyr | Gly | His | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Ser | Phe | Leu | Leu | Pro | Glu | Val | Gly | Arg | Gly | Leu | Pro | Asp | Leu | Ser |
|-----|-----|-----|-----|-----|-----|-----|-----|-----|-----|-----|-----|-----|-----|-----|-----|
|     |     |     |     | 20  |     |     |     | 25  |     |     |     |     | 30  |     |     |

| Pro | Asp | Gly | Gly | Ala | Asp | Pro | Val | Ala | Gly | Ser | Trp | Ala | Pro | His | Leu |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Leu | Ser | Glu | Val | Thr | Ala | Ser | Pro | Ala | Pro | Thr | Trp | Asp | Ala | Pro | Pro |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Asp | Asn | Ala | Ser | Gly | Cys | Gly | Glu | Gln | Ile | Asn | Tyr | Gly | Arg | Val | Glu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Lys | Val | Val | Ile | Gly | Ser | Ile | Leu | Thr | Leu | Ile | Thr | Leu | Leu | Thr | Ile |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Gly | Asn | Cys | Leu | Val | Val | Ile | Ser | Val | Cys | Phe | Val | Lys | Lys | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Arg | Gln | Pro | Ser | Asn | Tyr | Leu | Ile | Val | Ser | Leu | Ala | Leu | Ala | Asp | Leu |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ser | Val | Ala | Val | Ala | Val | Met | Pro | Phe | Val | Ser | Val | Thr | Asp | Leu | Ile |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Gly | Gly | Lys | Trp | Ile | Phe | Gly | His | Phe | Phe | Cys | Asn | Val | Phe | Ile | Ala |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Met | Asp | Val | Met | Cys | Cys | Thr | Ala | Ser | Ile | Met | Thr | Leu | Cys | Val | Ile |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ser | Ile | Asp | Arg | Tyr | Leu | Gly | Ile | Thr | Arg | Pro | Leu | Thr | Tyr | Pro | Val |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Arg | Gln | Asn | Gly | Lys | Cys | Met | Ala | Lys | Met | Ile | Leu | Ser | Val | Trp | Leu |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Leu | Ser | Ala | Ser | Ile | Thr | Leu | Pro | Pro | Leu | Phe | Gly | Trp | Ala | Gln | Asn |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Val | Asn | Asp | Asp | Lys | Val | Cys | Leu | Ile | Ser | Gln | Asp | Phe | Gly | Tyr | Thr |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ile | Tyr | Ser | Thr | Ala | Val | Ala | Phe | Tyr | Ile | Pro | Met | Ser | Val | Met | Leu |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Phe | Met | Tyr | Tyr | Gln | Ile | Tyr | Lys | Ala | Ala | Arg | Lys | Ser | Ala | Ala | Lys |
|-----|-----|-----|-----|-----|-----|-----|-----|-----|-----|-----|-----|-----|-----|-----|-----|

|         |         |         |         |         |         |     |         |         |         |         |         |         |         |
|---------|---------|---------|---------|---------|---------|-----|---------|---------|---------|---------|---------|---------|---------|
|         |         | 260     |         |         |         |     | 265     |         |         |         | 270     |         |         |
| His     | Lys     | Phe     | Pro     | Gly     | Phe     | Leu | Arg     | Val     | Glu     | Pro     | Asp     | Ser     | Val     | Ile | Ala |
|         |         | 275     |         |         |         |     | 280     |         |         |         | 285     |         |         |
| Leu     | Asn     | Gly     | Ile     | Val     | Lys     | Leu | Gln     | Lys     | Glu     | Val     | Glu     | Cys     | Ala     | Asn |
|         | 290     |         |         |         |         | 295 |         |         |         |         | 300     |         |         |
| Leu     | Ser     | Arg     | Leu     | Leu     | Lys     | His | Glu     | Arg     | Lys     | Asn     | Ile     | Ser     | Ile     | Phe | Lys |
| 305     |         |         |         |         | 310     |     |         |         |         | 315     |         |         |         |     | 320 |
| Arg     | Glu     | Gln     | Lys     | Ala     | Ala     | Thr | Thr     | Leu     | Gly     | Ile     | Ile     | Val     | Gly     | Ala | Phe |
|         |         |         |         | 325     |         |     |         |         | 330     |         |         |         | 335     |     |     |
| Thr     | Val     | Cys     | Trp     | Leu     | Pro     | Phe | Phe     | Leu     |         |         |         |         |         |     |     |
|         |         |         | 340     |         |         |     |         | 345     |         |         |         |         |         |     |     |

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TTTTTTTTT TTT					13

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TTTTTTTTT TTT					13

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

ACAAGTTTCC TGGCTTCCT					19

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GCTGCGATAG GTGGTCCTCA GGT					23